United States Patent [19]

Ayer

[11] 4,196,735

[45] Apr. 8, 1980

[54] ARTERIAL PUNCTURE STABILIZATION DEVICE

[76] Inventor: Patrick C. Ayer, Rte. 3, Woodridge Dr., Eau Claire, Wis. 54701

[21] Appl. No.: 832,568

[22] Filed: Sep. 12, 1977

[51] Int. Cl.² .................... A61B 17/12; A61M 5/00
[52] U.S. Cl. .......................... 128/327; 128/214 R; 128/215
[58] Field of Search ............... 128/214 R, 214.2, 215, 128/327, 325, 2 R, 2 A, 335, 346

[56] References Cited

U.S. PATENT DOCUMENTS

| | | | |
|---|---|---|---|
| 1,824,516 | 9/1931 | Tyvand | 128/327 |
| 2,185,571 | 1/1940 | Robinson | 128/327 |
| 2,238,323 | 4/1941 | Hollingsworth | 128/215 |
| 3,050,064 | 8/1962 | Moore et al. | 128/327 |
| 3,570,496 | 3/1971 | Sachs | 128/327 |
| 3,586,001 | 6/1971 | Sanderson | 128/327 |

Primary Examiner—Dalton L. Truluck
Attorney, Agent, or Firm—Merchant, Gould, Smith, Edell, Welter & Schmidt

[57] ABSTRACT

A device for stabilizing a blood vessel, in particular an artery, to facilitate the puncture of the vessel. The device includes a first member held in compressive contact against the skin by an elastic band encircling the patient's wrist. The device is oriented transversely with respect to the artery and has projecting leg members which engage the skin on opposite sides of the artery supplying pressure against the artery and tensioning the skin above the artery to stabilize the artery against its surrounding body tissues. A second member is provided to be captured between the first member and the wrist to cover and apply pressure to the arterial puncture to occlude the wound.

5 Claims, 5 Drawing Figures

ARTERIAL PUNCTURE STABILIZATION DEVICE

BACKGROUND OF THE INVENTION

The present invention relates broadly to a device for stabilizing a blood vessel to facilitate puncture of the vessel in order to extract blood therefrom or inject medication therein. In particular, the present invention is an arterial puncture stabilization device that facilitates arterial blood extraction.

The taking of arterial blood samples is recognized as an important feature in diagnosing and treating patients suffering from lung or heart diseases. In treating these patients, it is important to know that the oxygen content of the blood. Oxygen content is determined through blood gas analysis of arterial blood as opposed to venous blood. In extracting arterial blood samples, however, problems arise that are generally not present with respect to venous blood sampling. For example, prominent veins are located just beneath the skin and are readily visible. The physician or technician extracting venous blood, therefore, typically has no problem in locating the vein and puncturing the vein with a suitable extraction needle. On the other hand, arteries are typically located deeper in the body than veins making detection of the artery and insertion of a needle therein extremely difficult. Additionally, arterial blood is under significant pressure which has a tendency to cause the artery to wiggle or move within its tissue surroundings. Thus, it is difficult for the physician or technician to properly insert the extraction needle into the artery.

It is not uncommon for the physician or technician to miss the artery upon the first insertion of the needle. The needle may strike a vein adjacent the artery and the blood extracted therefrom would give an erroneous measure of arterial blood oxygen content. The needle may also strike a side wall of the artery tearing the vessel wall creating an aneurysm. If it is apparent to the physician or technician that the artery has not been properly punctured, the needle must be extracted and reinserted. The patient experiences considerably more pain due to multiple punctures and the risk of contamination with the second and subsequent punctures is significantly increased.

Additionally, once the arterial blood has been extracted, pressure must be maintained on the puncture wound for a considerably longer period of time than with venous extraction to allow the wound and artery to occlude. It is desirable to maintain even pressure on the arterial puncture wound for five minutes or more. Presently, the physician or technician must manually apply the desired pressure with the cotton or gauze pad. By its very nature, manual pressure application in this manner often results in uneven pressure and in addition consumes significant physician or technician time that could be occupied with more constructive tasks.

The present invention, therefore, eliminates the disadvantages of the prior arterial extraction methods in that it is a device for stabilizing the artery through the application of presssure on either side of the artery. The device is secured to the patient's wrist from which arterial blood is typically sampled by a stretched rubber or elastic band encircling the wrist such that pressure is applied to the skin above an artery location. The pressure applied holds the artery against the surrounding tissue essentially preventing movement of the artery. The actual puncture location is determined by manually detecting the pulse in the artery, and the puncture is made proximate the stabilization device. The probability of properly puncturing the artery upon the first insertion of the needle is substantially increased utilizing the present invention. Further, the present invention includes an apparatus which is placed over the puncture wound following extraction of the arterial blood sample and retained until the wound is occluded properly by the compressive force of the elastic band.

SUMMARY OF THE INVENTION

The present invention is a device for stabilizing a blood vessel within a limb so that the vessel may be punctured. The device is secured about the limb by an elastic band encircling the limb and includes a substantially planar first member with top and bottom surfaces. The device includes means projecting from the bottom surface of the planar first member for contacting the limb about the vessel location and applying pressure to the limb to stabilize the vessel. Means affixed to the first member provides for attachment to the elastic band to secure the first member in compressive contact against the limb whereby the vessel is stabilized for puncture made proximate the device.

In the preferred embodiment, the present invention is an arterial puncture stabilization device in which the planar first member has a pair of downwardly projecting leg members affixed to the bottom surface of the first member and which are spaced apart a pre-determined distance whereby the device may be positioned on the wrist of a patient tranversely with respect to an artery with the artery disposed between the leg members. The application of pressure to the wrist is through the leg members which tend to tension or stretch the skin in addition to stabilizing the artery beneath the skin against its surrounding body tissues. The means for attaching the elastic band to the first member includes a pair of arms extending from the top surface of the first member each of which is engaged by opposite ends of the elastic band encircling the wrist.

A second substantially planar member having top and bottom surfaces and a pair of slots therein to receive the leg members of the first member is provided for insertion between the first member and the skin following extraction of the arterial blood sample. The second member has a pad of absorbent sterile material affixed to its bottom surface to cover and apply pressure to the puncture wound.

The device with the second member in place covering the puncture wound can be left unattended for the desired period of time required for the wound and artery to occlude. The physician or technician is thereby freed for other more meaningful tasks. In the preferred embodiment, the stabilization device is molded of a suitable plastic material and is designed to be disposable following a single use.

From the above description, it can be appreciated that the present invention is a device that facilitiates puncture of blood vessels, particularly arteries, and substantially eliminates the problems discussed above that develop when the needle is not properly inserted into the vessel. The simplicity of design and construction of the present invention is an important and unique feature making it compatible with the modern medical trend toward disposable, presterilized, and low cost products. These and other advantages of my invention will become apparent with reference to the accompany-

DETAILED DESCRIPTION OF THE PREFERRED EMBODIMENT

Figure 1:
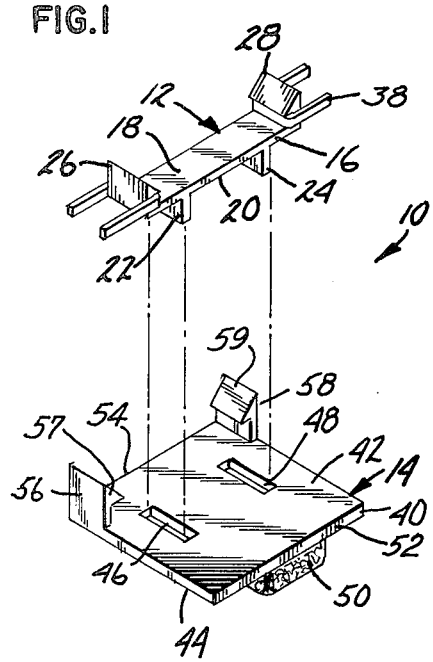
FIG. 1 is an exploded view in perspective of the preferred embodiment of the stabilization device of the present invention.

Referring to the drawing, wherein like numerals represent like parts throughout the several views, the arterial puncture stabilization device of the present invention is designated generally as 10. Device 10 includes a first member 12 and a second member 14 that may be releasably attached to each other as will be described in more detail hereafter. First member 12 includes a substantially planar rectangular base member 16 having a top surface 18 and a bottom surface 20. Projecting downwardly from bottom surface 20 and affixed thereto are a pair of spaced leg members 22 and 24. Extending upwardly and outwardly with respect to the top surface 18 are a pair of arm portions 26 and 28 affixed to base member 16. Arm portions 26 and 28 are preferably disposed at opposite ends of base member 16. Arm portions 26 and 28 have lips 30 and 32 which extend above top surface 18 of base member 16 to define a channel or groove 34 and 36 in which ends of an elastic band 38 is captured. As illustrated in more detail in FIGS. 2—5, elastic band 38 encircles the patient's limb holding first member 12 in compressive engagement against the skin.

Second member 14 includes a substantially planar base member 40 having a top surface 42 and a bottom surface 44. A pair of elongated slots 46 and 48 are provided in base member 40 and are spaced apart to receive leg members 22 and 24 therein. Affixed to bottom surface 44 of base member 40 by any suitable means is a pad 50 of sterile gauze or other suitable material. Pad 50 extends along bottom surface 44 from an end 52 of base member 40 to an opposite end 54. Pad 50 has a lateral dimension smaller than the distance between slots 46 and 48 so that pad 50 will not interfere with the insertion of leg members 22 and 24 through slots 46 and 48. Projecting outwardly with respect to top surface 42 and affixed to base member 40 is a pair of arms 56 and 58. Arms 56 and 58 are disposed proximate end 54 of base member 40 and provide convenient means for manually grasping second member 14. Arms 56 and 58 are somewhat flexible and have lips 57 and 59 projecting above top surface 18. Base member 40 is sized substantially larger than base member 16 as is readily apparent in FIG. 1 and FIG. 4.

Figure 2:
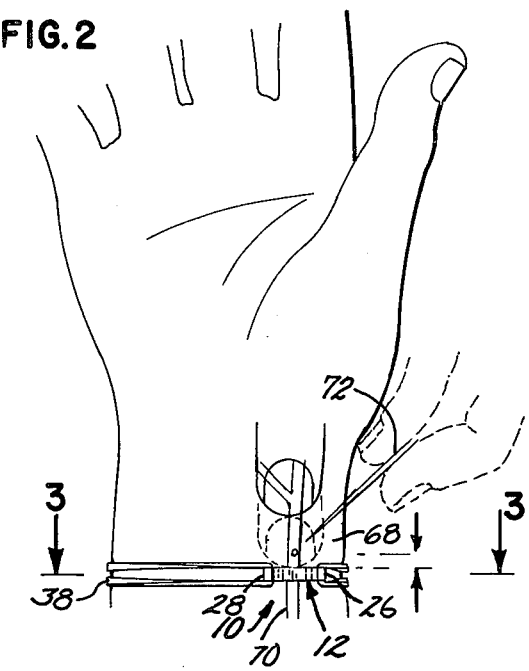
FIG. 2 is a view in elevation showing the application of the present invention in arterial blood extraction from a patient's wrist.
Figure 3:
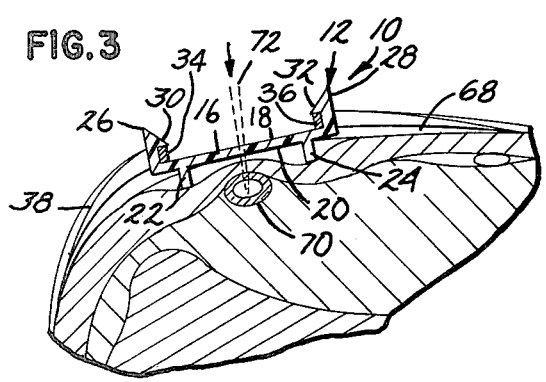
FIG. 3 is an enlarged fragmentary sectional view taken generally along the line 3—3 of FIG. 2.

The operation of the present invention will now be described with particular reference to FIGS. 2-5. As shown in FIGS. 2-3, first member 12 is secured to the patient by an elastic band 38 which encircles the patient's wrist and has opposite ends captured within grooves 34 and 36. First member 12 is oriented transversely with respect to an artery 70. As illustrated in FIG. 3, leg members 22 and 24 contact the surface 68 of the skin at contact points on either side of artery 70. Since elastic band 38 is stretched, member 12 through leg members 22 and 24 applies compressive force against the skin. This compressive force is transmitted by the skin and body tissues to artery 70. Under this compressive force artery 70 is stabilized against the tissue surrounding it. The artery is thereby held in a substantially fixed position to facilitate the insertion of a needle therein. Additionally, skin above the arterial position is stretched by the application of compressive force by leg members 22 and 24. The skin is therefore tensioned over the artery and also maintained in a stable position for insertion of a needle. The tendency of the skin and artery to slide out of the proper orientation for insertion of a needle is thereby substantially eliminated by the present invention.

A needle 72 is preferably inserted approximately ⅛ of an inch from first member 12. The physician or technician typically feels for the pulse proximate first member 12 with his index finger as shown in dashed lines in FIG. 3. When the pulse is detected, the physician or technician moves his index finger to the position shown in solid lines in FIG. 3 and inserts needle 72 into the stabilized artery for extraction of blood therefrom. Utilizing stabilization device 10 in this manner there is a substantial probability that artery 70 will be properly punctured upon the initial insertion of needle 72 into the patient. Device 10 facilitates location of the artery within the tissues of the wrist in addition to retaining artery 70 in a stabilized position.

When the desired amount of blood has been extracted from the artery, needle 72 is removed. It is then important to apply pressure to the puncture wound to stop the flow of blood therefrom and allow the wound and artery to heal. Pressure must be maintained on the wound for a longer period of time than in the case of a vein punctures since the pressure of the blood within the artery is significant. Therefore, when needle 72 is removed, the physician raises first member 12 from the skin surface and slides second member 14 between first member 12 and the skin 68 until leg members 22 and 24 are received within slots 46 and 48. Typically, the physician places his index finger between arms 56 and 58 into contact with top surface 18 to slide second member 14 under first member 12. If the physician's index finger is wider than the distance between arms 56 and 58, the arms will be biased outward, thereby compressively engaging the index finger. On the other hand, if the index finger is smaller than the distance between arms 56 and 58, lips 57 and 59 grip the index finger to secure it within arms 56 and 58 facilitating insertion of second member 14 between first member 12 and skin 68. Second member 14 can, therefore, be easily manipulated with index finger of one hand. The physician may then release first member 12 and elastic band 38 will function to maintain a compressive force against the skin through second member 14.

Figure 4:
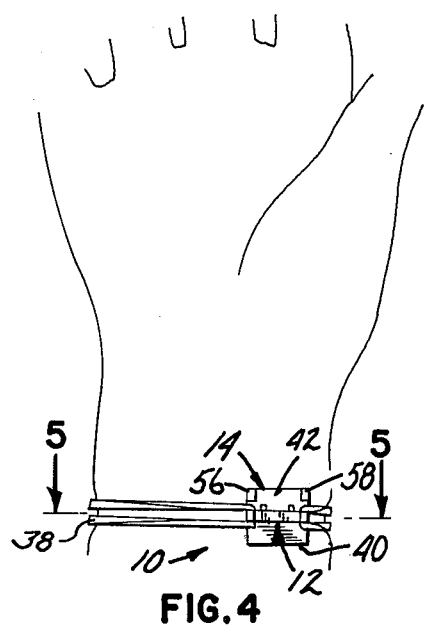
FIG. 4 is a view in elevation showing the present invention in place on the patient's wrist following the arterial blood extraction.
Figure 5:
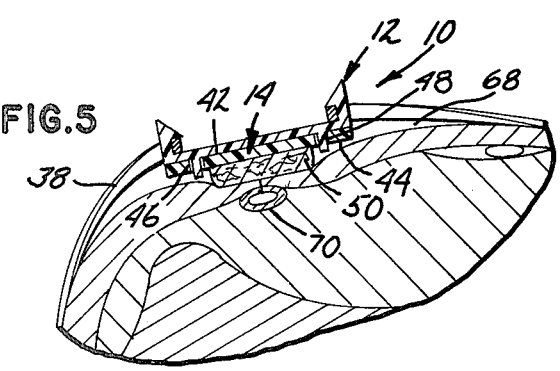
FIG. 5 is an enlarged fragmentary sectional view taken generally along line 5—5 of FIG. 4.

FIGS. 4 and 5 illustrate second member 14 held in compressing contact against skin 68 by first member 12 and elastic band 38. Base member 40 of second member 14 is substantially larger than base portion 16 of first member 12. As shown in particular in FIG. 4, the puncture wound will be covered by pad 50 that extends between ends 52 and 54 of base portion 40. Stabilization device 10 therefore provides uniform pressure over the puncture wound to stop blood loss from the wound and allow the artery to heal. The physician can simply leave stabilization device 10 on the patient until he is satisfied that the arterial puncture has been occluded. It is preferable to leave stabilization device 10 in place with second member 14 applying pressure to the puncture wound for at least five minutes. The use of stabilization device 10 in this manner allows the physician or technician to proceed with other tasks. The physician or technician does not have to manually apply pressure to the puncture wound for the required time period.

In the preferred embodiment, first member 12 and second member 14 of stabilization device 10 are molded of a suitable plastic material and may be simply discarded after a single use. Stabilization device 10 is relatively easy and inexpensive to manufacture.

From the above description, it can be appreciated that the present invention is an easy to use disposable stabilization device for blood vessel, in particular for arterial punctures. The stabilization device is secured to the patient's wrist by commercially available elastic bands and applies pressure at the artery location. The artery and skin are thereby held against any tendency to slide or move during puncture. Thus the probability of properly puncturing the artery upon the first needle insertion is significantly increased reducing the potential damage, not to mention pain experienced by the patient, that might result from missing the artery upon the first insertion thereby requiring additional punctures. The present invention also includes structure for applying pressure to the puncture wound after the blood has been drawn from the patient without constant attention by the physician or technician. Pressure is maintained on the puncture wound for sufficient time to allow the wound to occlude.

I claim:

1. A device for stabilizing a blood vessel within a limb so that the vessel can be punctured, said device adapted to be secured about the limb by an elastic band circling the limb, comprising:
   (a) a substantially planar first member having top and bottom surfaces;
   (b) means projecting from said bottom surface of said first member for contacting the limb about the location of the vessel applying pressure to the limb to stabilize the vessel;
   (c) means affixed to said first member to which the elastic band is attached for securing the said first member in compressive contact against the limb;
   (d) a second member for occluding the puncture made in the limb and the vessel, said second member comprising a substantially planar member with top and bottom surfaces, said second member sized larger than said first member to cover the puncture wound made proximate said first member;
   (e) said second member further comprising means for releasably engaging said projecting means of said first member to secure said second member to said first member with said top surface of said second member engaging said bottom surface of said first member.

2. A device in accordance with claim 1 wherein said projecting means comprises a pair of downwardly extending leg members affixed to said bottom surface of said first member and spaced apart thereon whereby said device may be positioned on said limb transversely with respect to said vessel with said vessel disposed between said leg members, and wherein said planar member of said second member has a pair of slots spaced apart to receive said leg members.

3. A device in accordance with claim 1 wherein said second member further comprises a pad of absorbent sterile material affixed to said bottom surface thereof to cover said puncture wound.

4. A device in acordance with claim 1 wherein said second member further comprises a pair of resilient arm members spaced apart on said planar member and extending upwardly from said top surface of said planar member whereby said second member may be grasped by placing one finger between said arm members.

5. An arterial puncture stabilization device secured to a patient's wrist by an elastic band to stabilize an artery which is to be punctured for blood extraction, comprising:
   (a) a substantially planar first member having top and bottom surfaces;
   (b) a pair of downwardly projecting leg members affixed to said bottom surface and spaced apart a predetermined distance whereby said device may be positioned on the wrist transversely with respect to the artery with the artery disposed between said leg members;
   (c) a pair of upwardly extending arm members affixed at opposite ends of said first member, each arm member adapted to be engaged by opposite ends of the elastic band encircling the wrist whereby said first member is secured in compressive engagement against the wrist with said downwardly projecting leg members contacting the wrist about said artery;
   (d) a substantially planar second member having top and bottom surfaces and a pair of slots therein sized to receive said leg members of said first member;
   (e) a pad of absorbant sterile material affixed to said bottom surface of said second member; and
   (f) whereby said second member may be inserted between said first member and the wrist with said leg members received within said slots in said second member and said pad covering the puncture in said wrist and applying the pressure thereto.

* * * * *